United States Patent [19]

Devon et al.

[11] Patent Number: 4,824,977
[45] Date of Patent: Apr. 25, 1989

[54] CHELATING LIGANDS AND CATALYSTS AND PROCESSES EMPLOYING THE SAME

[75] Inventors: Thomas J. Devon; Gerald W. Phillips; Thomas A. Puckette; Jerome L. Stavinoha, Jr.; Jeffrey J. Vanderbilt, all of Longview, Tex.

[73] Assignee: Eastman Kodak Company, Rochester, N.Y.

[21] Appl. No.: 166,936

[22] Filed: Mar. 11, 1988

Related U.S. Application Data

[62] Division of Ser. No. 41,968, Apr. 24, 1987, Pat. No. 4,774,362.

[51] Int. Cl.$^4$ .......................... C07F 15/00; C07F 9/50
[52] U.S. Cl. ......................................... 556/21; 556/15; 556/17; 556/19; 568/10; 568/17; 568/454
[58] Field of Search ...................... 556/21, 19; 568/10, 568/454

[56] References Cited

U.S. PATENT DOCUMENTS 4,229,381 10/1980 Ogata et al. .......................... 568/454
4,593,141  6/1986 Oswald et al. ....................... 568/454
4,755,624  7/1988 Phillips et al. ...................... 568/454

Primary Examiner—Werren B. Lone
Attorney, Agent, or Firm—S. E. Reiter; William P. Heath, Jr.

[57] ABSTRACT

A hydroformylation process including contacting hydroformylation stock in a reaction zone at a temperature of from about 20° C. to about 250° C. and a pressure of from about 15 psig to about 800 psig with hydrogen and carbon monoxide wherein the catalyst comprises rhodium in chemical complex with one or more ligands of the formulae

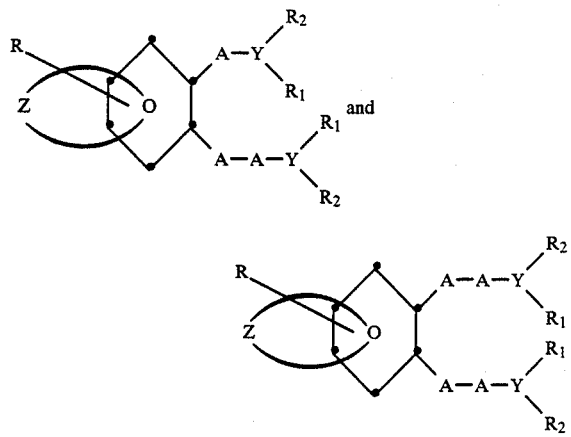

wherein:

Z, when present, represents the atoms necessary to form with adjacent carbons on the benzene nucleus a fused divalent ring structure having up to about 20 ring carbons;

each ring is either unsubstituted or one or more of the hydrogens thereof is replaced with a substituent R selected independently from alkyl, alkoxy, aryloxy, aryl, aralkyl, alkaryl, alkoxyalkyl, cycloaliphatic, halogen, alkanoyl, alkanoyloxy, alkoxycarbonyl, carboxyl or cyano;

each $R_1$ and $R_2$ is selected independently from alkyl, aryl, aralkyl, alkaryl or cycloaliphatic;

each A is a carbon atom which is either unsubstituted or substituted with one or two independently selected R substituents;

each of the above hydrocarbon groups or moieties of R, $R_1$ or $R_2$ may be substituted with 1-3 of the aforesaid R substituents;

each of the above alkyl groups or moieties is straight or branched chain of 1-20 carbons, preferably 1-8 carbons, each aryl group contains 6-10 ring carbons, and each cycloaliphatic group contains from 4-6 ring carbons; and each Y is independently selected from the elements N, P, As, Sb and Bi.

6 Claims, No Drawings

CHELATING LIGANDS AND CATALYSTS AND PROCESSES EMPLOYING THE SAME

This is a divisional of application Ser. No. 041,968, filed on Apr. 24, 1987, now U.S. Pat. No. 4,774,362.

FIELD OF THE INVENTION

This invention concerns novel chelating ligands and catalysts and processes employing the same such as hydroformylation catalysts and processes wherein one or more olefins and/or non-conjugated diolefins, and/or other unsaturated organic compounds, all hereinafter referred to as hydroformylation stock, may be converted to aldehydes for use as such or for conversion by known methods to products such as alcohols and acids.

BACKGROUND OF THE INVENTION

More particularly, the invention concerns chelating diphosphino ligands especially useful for oxo or hydroformylation processes designed for relatively low pressure operation for the preparation of unusually high proportions of normal or unbranched aldehydes from α-olefins, particularly n-butyraldehyde from propylene.

The use of the present ligands in the rhodium catalyzed hydroformylation of olefins offers significant advantages over the use of monodentate ligands such as triphenylphosphine in that only small quantities of bidentate ligand are required for obtaining high selectivity to linear aldehyde product. By contrast, high concentrations of costly monodentate triarylphosphine ligands are required in order to obtain similar selectivity thus incurring high capital costs.

The present ligands are compounds of the general formulae

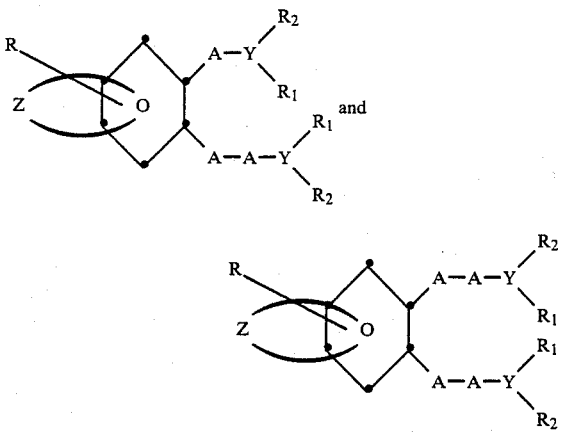

wherein:

Z, when present, represents the atoms necessary to form with adjacent carbons on the benzene nucleus a fused divalent ring structure having up to about 20 ring carbons, preferably, said fused ring structure being selected from divalent naphthalene, anthracene, phenanthrene, pyrene, perylene, fluorene, quinoxaline, quinoline, isoquinoline, benzothiophene, benzofuran, benzoxazole, benzothiazole, benzimidazole, 5,6-benzoquinoline, 7,8-benzoquinoline, 1,2-benzisoxazole, or 2,1-benzisoxazole;

each ring is unsubstituted or substituted with up to three R substituents selected independently from alkyl, alkoxy, aryloxy, aryl, aralkyl, alkaryl, alkoxyalkyl, cycloaliphatic, halogen, alkanoyl, alkanoyloxy, alkoxycarbonyl, carboxyl or cyano;

each $R_1$ and $R_2$ is selected independently from alkyl, aryl, aralkyl, alkaryl or cycloaliphatic;

each A is a carbon atom which is either unsubstituted or substituted with one or two independently selected R substituents;

each of the above hydrocarbon groups or moieties of R, $R_1$ or $R_2$ may be substituted with 1-3 of the aforesaid R substituents;

each of the above alkyl groups or moieties is straight or branched chain of 1-20 carbons, preferably 1-8 carbons, each aryl group contains 6-10 ring carbons, and each cycloaliphatic group contains from 4-6 ring carbons; and each Y is independently selected from the elements N, P, As, Sb and Bi, with P being preferred.

In a particular embodiment of the present invention we have discovered that the above structural arrangements of two phosphorus atoms in that particular spatial arrangement, when coordinated to rhodium carbonyl under hydroformylation conditions promotes the formation of linear aldehyde products to an exceptional degree. This feature allows more efficient use of olefinic feedstocks for the preparation of the desired linear aldehyde products. Thus, the hydroformylation of propylene gives normal butyraldehyde, a precursor for the valuable solvent n-butanol, and 2-ethylhexanol, an ingredient in plasticizers. The hydroformylation of 1-pentene and 1-butene gives precursors of the solvents 1-hexanol and n-amyl alcohol. In the hydroformylation of 1-hexene and 1-octene carried out on a commercial scale, this invention would permit the preparation of heptanal and nonanal with a high selectivity to linear isomers that would lead to the corresponding alcohol and carboxylic acid end products having utility for the preparation of plasticizers, synthetic lubricants, and detergents. The hydroformylation of 1-decene and 1-dodecene would lead ultimately to the preparation of 1-undecanol and 1-hydroxytridecane which are useful as fabric softeners, and as ingredients for plasticizers and detergents.

Likwise, the present ligands would have substantial utility in the promotion of certain other transition metal catalyzed reactions such as in combination with platinum and Group IVA metals such as tin where other chelating diphosphine ligands as disclosed in U.S. Pat. No. 4,229,381 have been employed in the hydroformylation of olefins.

It is within the scope of this invention that substituent groups can be attached to the aromatic side chains on the carbons to which the phosphorus atoms are attached, thereby forming diasteriomeric and enantiomeric ligand mixtures which if resolved into optical isomers by means available in the art, would lead to chiral ligands. Such optically active chelate ligands would have utility in asymmetric hydroformylation reactions and would also have utility in the rhodium catalyzed asymmetric hydrogenation of substituted acrylic acid derivatives useful as drug intermediates for the synthesis of R-(—)-pantolactone (see K. Achiva, et. al., Chem. Lett., 297 (1978) and for the hydrogenation of itaconic acid (see K. Achiva, et. al., Tet. Lett., 1475 (1978). Chirality of these ligands is also obtainable by the use of two different hydrocarbyl groups attached to the tetrahedral phosphorus atoms, such as bis(phenyl-n-butylphosphino) diphosphine chelate ligands, which could also be resolved into optical isomers through means known in the art.

The ligands of this invention also would find utility in the nickel catalyzed cross coupling reactions of Grignard reagents with aryl and vinyl halides, a reaction which has been carried out with similar chelating diphosphine ligands as disclosed by K. Yamamoto, et. al., Tet. Lett. 3 (1974) and M. Kumada, et. al., J. Amer. Chem. Soc., 98, 3718 (1976).

The present hydroformylation process in its broad sense comprises contacting at least one olefin having from 2 to about 20 carbon atoms in a reaction zone at a temperature of from about 20° C. to about 250° C. and a pressure of from about 15 psig to about 800 psig with syn gas ($H_2$, CO) and a catalyst comprising rhodium in chemical complex with one or more of the above chelating diphosphino ligands for a sufficient period of time to permit reaction of said olefin with said syn gas to form aldehyde product.

The present ligands, in particular, those of Examples 2, 3, 4, 5, 7, 8, 9 and 10 of TABLE I below have special utility as a bidentate ligand modifier for the low pressure rhodium hydroformylation of alpha-olefins to prepare aldehyde products with unusually high ratios of normal to branched isomers in high yield. Such products from propylene include n-butyraldehyde which is used to prepare the commercial solvent n-butanol. The hydroformylation of 1-butene and 1-pentene yield intermediate aldehyde products useful for the preparation of the solvents 1-pentanol and 1-hexanol, respectively. The hydroformylations of 1-hexene and 1-octene yield aldehyde products used to prepare the commercially valuable carboxylic acids, n-heptanoic acid and n-nonanoic acid. These same aldehyde products may be converted into alcohols useful for the preparation of plasticizers, synthetic lubricants, and detergents. Likewise, the hydroformylation of higher olefins such as 1-decene and 1-dodecene yield aldehyde precursors to 1-undecanol and 1-hydroxytridecane useful as fabric softeners and ingredients in plasticizers and detergents. These ligands show improvements in hydroformylation technology in one or more areas such as the production of high normal to iso ratios employing relatively small amounts of ligand, increased conversions in low pressure systems, increased catalytic activity and retention thereof over extended periods, and increased catalyst stability.

As a general statement of the actual chemical composition of the present active catalyst species in the reaction zone, the species preferably comprises rhodium complexed with (a) a ligand defined by either of the above structural formulae in a molar ratio of ligand/Rh of about 1/1, (b) H in an atomic ratio of H/Rh of about 1/1, and (c) carbon monoxide in a molar ratio of CO/Rh of about 2/1.

Of the Group VA elements, phosphorus is the preferred for this invention. Of the "$R_1$" and "$R_2$" hydrocarbon groups, aryl is preferred for both groups yielding the highest selectivity to linear product aldehydes under low pressure rhodium hydroformylation conditions. High selectivities to linear isomer product are also observed if "$R_1$" alone is aryl. Selectivity to linear aldehyde product is generally reduced by attaching alkyl or aryl groups to the carbon atoms directly bound to the phosphorus atom.

There are many synthetic routes available to obtain the present ligands and the following examples illustrate some of the routes available to one skilled in the art. The ortho ethyl toluene composition is readily available synthetically from homophthalic acid, a derivative of indene. The following examples are illustrative of the preparation and use of the present ligands and are not intended to limit the invention in any manner. The table below lists the structures given in the examples, and any name abbreviation thereof.

TABLE I

| Example | Structure | Abbreviation |
|---|---|---|
| 1 | (Intermediate) benzene ring with Br, Br substituents | BMBEB |
| 2 | benzene ring with $P\phi_2$, $P\phi_2$ substituents | BISHOP |
| 3 | benzene ring with $PBz_2$, $PBz_2$ substituents | BENHOP |
| 4 | benzene ring with P($\phi$)(Bz), P($\phi$)(Bz) substituents | PBENHOP |
| 5 | benzene ring with P($\phi$)(butyl), P($\phi$)(butyl) substituents | PBUTHOP |
| 6 | (Intermediate) benzene ring with Br, Br substituents | BEB |
| 7 | benzene ring with $P\phi_2$, $P\phi_2$ substituents | DIPEB |
| 8 | benzene ring with $PBz_2$, $PBz_2$ substituents | BENPEB |

TABLE I-continued

| Example | Structure | Abbreviation |
|---|---|---|
| 9 | benzene ring with CH(Pφ₂)- and -CH(CH₃)Pφ₂ substituents | |
| 10 | benzene ring with CH(PBz₂)- and -CH(CH₃)PBz₂ substituents | |

EXAMPLE 1

Preparation of α,β'-Dibromo-2-ethyltoluene (BMBEB)

A 100-mL three-necked flask was equipped with a reflux condenser, magnetic stir bar, and thermometer. The flask was charged with phosphorus tribromide (8.9 grams, 32.9 mmole) in 40 mL of toluene solvent and then cooled to 15° C. A solution of 2-hydroxymethyl(2'-hydroxyethyl)benzene (5.0 grams, 32.9 mmole) in 25 mL of toluene was added to the stirred mixture at 15° C. This mixture was stirred at 0° C. to 15° C. for 30 minutes and then heated to reflux for 1 hour. The mixture was extracted with three 100 mL portions of dichloromethane. The combined organic phases were washed with 100 mL of water. The organic solution was dried with anhydrous magnesium sulfate and filtered. The volatile solvents were removed on a rotary evaporator at 40° C. at 10 torr to leave 4.9 grams of crude product which was purified by bulb to bulb distillation at 150° C. at 1 torr to give 4.6 grams of product which analyzed as follows:

$^1$H NMR (CDCl$_3$)δ: 3.00–3.77 (4H, complex); 4.40 (2H, singlet); 7.00 (4H, singlet).

EXAMPLE 2

Preparation of α,β'-Bis(diphenylphosphino)-2-ethyltoluene (BISHOP)

The apparatus was a 500-mL three-necked flask equipped with a mechanical stirrer, thermometer, pressure equalizing dropping funnel, and a nitrogen atmosphere. The flask was charged with 200 mL of dry tetrahydrofuran (THF) and diphenylphosphine (4.0 gram, 21.6 mmole) and cooled to −78° C. N-Butyllithium (1.55 molar, 13.9 mL, and 21.6 mmole) in hexane was added dropwise to the cold solution. The resulting orange solution was warmed to 0° C. for 1 hour and then cooled back down to −78° C. A solution of BMBEB of Example 1 (3.0 grams, 10.8 mmole) in 25 mL of THF was added to the cold mixture dropwise from the dropping funnel over 30 minutes. The mixture was stirred at −78° C. for an additional 2 hours and then warmed to 25° C. and stirred for an additional 30 minutes. Water (2 mL) was added to quench the reaction. The mixture was warmed to 70° C. and swept with a stream of argon to strip away the volatile components. Toluene (200 mL) and water (100 mL) were added to the resulting oil which was briefly heated to reflux to solubilize the mixture. The two layers were separated and the organic layer was stripped under argon (70° C.,
100 torr) to give 5.5 grams of the product as a white solid analyzing as follows:

$^1$H NMR (CDCl$_3$)δ: 2.00–2.83 (4H, complex); 3.16 (2H, singlet); 6.50–7.50 (24H, complex);

$^{31}$P NMR (CDCl$_3$)δ: +14, +11 PPM (Relative to 85 Percent Aqueous H$_3$PO$_4$).

EXAMPLE 3

Preparation of α,β'-Bis(dibenzylphosphino)-2-ethyltoluene (BENHOP)

Dibenzylphosphine oxide (6.62 grams, 28.8 mmole) was dissolved in 100 mL of dry THF in a 250-mL three-necked flask, and cooled to −50° C. under nitrogen. N-Butyllithium (1.6 molar in hexane, 18 mL, 28.8 mmole) was added dropwise over 15 minutes. This mixture was stirred at −40° C. to −60° C. for an additional hour. A solution was prepared from BMBEB (3.5 grams, 14.0 mmole) in 40 mL of THF and contained in a dropping funnel. This solution was added to the above mixture dropwise at room temperature and the mixture was refluxed for 1 hour and cooled. The crude mixture was treated with 1 mL of water and heated on a steam bath with a nitrogen sweep to remove solvent. The residue was dissolved in dichloromethane and subsequently washed with water and aqueous sodium chloride solution. The organic layer was dried over anhydrous magnesium sulfate. The organic phase was filtered from the magnesium salts and concentrated by evaporation to yield a solid residue of the crude BENHOP dioxide. This solid was triturated with diethyl ether yielding 6.4 grams, 79 percent yield, of the BENHOP dioxide.

The BENHOP dioxide was reduced to the desired ligand by the following procedure of E. P. Kyba et al, *Organometallics*, 2, 1977 (1983), and E. P. Kyba, et al, *Inorganic Chemistry*, 24, 1613 (1985). Trimethylchlorosilane (2.73 mL, 21.5 mmole) was added to a mixture of lithium aluminum hydride (0.79 gram, 20.8 mmole) in THF at −78° C. under nitrogen. After warming to room temperature, this mixture was stirred an additional 2 hours. A separate solution of BENHOP dioxide (4.0 grams, 6.94 mmole) in 50 mL of THF was cooled to −78° C. under nitrogen. The lithium aluminum hydride mixture mentioned above was added to this ligand dioxide mixture at −78° C. The mixture was warmed to room temperature and stirred at room temperature for an additional 16 hours. Water (0.79 mL), 15 percent aqueous sodium hydroxide (0.79 mL) and additional water (2.37 mL) were added sequentially. The organic mixture was filtered from the salts and concentrated on a steam bath with a nitrogen sweep. The mixture was transferred to a Kugelrohr apparatus and was heated to 230° C. under 1.5 torr to remove lower boiling impurities from the nonvolatile product. The product (2.3 grams, 61 percent yield) was a viscous oil analyzing as follows:

$^1$H NMR (CDCl$_3$)δ: 1.2–1.8 (multiplet, 2H); 2.3–3.1 (multiplet, 12H); 6.5–7.3 (multiplet, 24H);

$^{31}$P NMR (CDCl$_3$)δ: +14, +15 PPM (Relative to 85 Percent H$_3$PO$_4$).

EXAMPLE 4

Preparation of
α,β'-Bis(phenyl,benzylphosphino)-2-ethyltoluene
(PBENHOP)

Benzyldiphenylphosphine (7.95 grams, 28.8 mmole) was dissolved in 50 mL of THF under an argon atmosphere. Lithium wire (0.40 gram, 57 mmole) was cut into small pieces and added to a 100 mL flask under argon with 0.04 gram naphthalene and 30 mL of THF. The phosphine compound was added to the lithium mixture and was stirred at 40° C. for 6 hours. The resulting dark red solution was cooled to room temperature and treated with 2.0 mL of t-butylchloride. After 10 minutes, a solution of BMBEB (2.97 grams, 10.7 mmole) in THF was added at room temperature. This mixture was then heated to reflux for 30 minutes and then cooled to room temperature. Water (5 mL) was added, and the mixture heated on a steam bath with a nitrogen sweep to remove solvent. After cooling to room temperature, the mixture was dissolved in diethyl ether and washed with water to remove lithium salts. The ether was removed by heating on a steam bath with a nitrogen sweep. The crude product was transferred to a Kugelrohr apparatus and heated to 230° C. at 0.7 torr to remove lower boiling impurities. The resulting product was a white solid (4.03 gram, 73 percent yield) analyzing as follows:

$^1$H NMR (CDCl$_3$)δ: 2.0–3.3 (multiplet, 10H); 6.5–7.5 (multiplet, 24H);

$^{31}$P NMR (CDCl$_3$)δ: +11, +15 PPM (Relative to 85 Percent H$_3$PO$_4$).

EXAMPLE 5

Preparation of α,
β'-Bis(n-butyl,phenylphosphino)-2-ethyltoluene
(PBUTHOP)

This compound was prepared by a procedure very similar to that of Example 4. Thus, butyldiphenylphosphine (6.0 grams, 24.8 mmole) was reacted with lithium (0.38 gram, 54 mmole) in the presence of 0.06 gram of naphthalene and was treated with 1.7 mL of t-butyl chloride followed by reaction with BMBEB (3.25 grams, 11.7 mmole). The product was obtained as a glass after the Kugelrohr treatment (2.87 grams, 55 percent yield) analyzing as follows:

$^1$H NMR (CDCl$_3$)δ: 0.6–2.8 (multiplet, 10H); 6.5–7.5 (multiplet, 24H);

$^{31}$P NMR (CDCl$_3$)δ: +19, +22.0, +22.5 PPM (Relative to 85 Percent H$_3$PO$_4$).

EXAMPLE 6

Preparation of 1,2-Bis(2-bromoethyl)benzene (BEB)

This compound was prepared from 1,2-phenylene diacetic acid in two steps; (1) reduction of the diacid with lithium aluminum hydride to the corresponding diol and (2), conversion of the diol to the dibromide with phosphorus tribromide. The general methods for these two steps are given in the following Examples A and B respectively.

EXAMPLE A

Lithium aluminum hydride (0.332 mol) and tetrahydrofuran (THF, 175 mL) are placed in a dry 500-mL three-necked round-bottom flask fitted with a condenser, addition funnel, nitrogen inlet, and magnetic stirrer. The mixture is cooled with an ice bath and 1,2-phenylene diacetic acid (0.165 mol) in THF (100 mL) is added dropwise to the stirring mixture. After the addition is complete, the flask is removed from the ice bath and allowed to warm to room temperature. The reaction mixture is heated at reflux for two hours, then stirred overnight at room temperature. After cooling the mixture with an ice bath, water (12.6 mL) is added dropwise, followed by the successive dropwise addition of 15 percent aqueous sodium hydroxide (12.6 mL) and water (38 mL). The resulting mixture is warmed to room temperature, and the solids separated by vacuum filtration. The filtrate is placed on a rotary evaporator to remove the solvent. The remaining solid is recrystallized from toluene-hexane to give the 1,2-di(hydroxyethyl)benzene.

EXAMPLE B 1,2-Di(hydroxyethyl)benzene (0.117 mol) and methylene chloride (200 mL) are placed in a 500-mL round-bottomed flask equipped with a magnetic stirrer and an addition funnel with a CaCl$_2$ drying tube. The stirred mixture is cooled with an ice bath, and phosphorus tribromide (23.1 mL, 66.50 grams, 0.246 mol) is added dropwise from the addition funnel. After the addition is complete, the reaction mixture is removed from the ice bath and stirred overnight at room temperature. The mixture is again cooled with an ice bath, and water (35 mL) is added slowly. After stirring for one hour, additional water (75 mL) is added. The layers are separated in a separatory funnel, and the aqueous layer extracted twice with CH$_2$Cl$_2$. The combined organic layer is washed with saturated aqueous NaHCO$_3$ and water and then dried (MgSO$_4$). The solvent is removed on a rotary evaporator to give the 1,2-di(bromoethyl)benzene.

Thus, the intermediate diol was prepared from 1,2-phenylene diacetic acid in 81 percent yield and the dibromo compound from the diol in 44 percent yield analyzing as follows:

$^1$H NMR δ: 2.8–3.7 (multiplet 8H); 7.0 (singlet 4H).

EXAMPLE 7

Preparation of
1,2-Bis[2-(diphenylphosphino)ethyl]benzene (DIPEB)

THF (100 mL) was added to a 300-mL flask and then was cooled to −50° C. under nitrogen. Diphenylphosphine (3.72 grams, 20 mmole) was added via syringe. N-Butyl lithium solution in hexane (12.5 mL of 1.6 molar solution, 20 mmole) was added dropwise via syringe. The mixture was warmed to 0° C. and then cooled back to −65° C. A solution of BEB (2.92 grams, 10 mmole) of Example 6 in 20 mL of THF was added dropwise via syringe. This was warmed to reflux and kept at reflux for 1 hour. After cooling, 5 mL of water was added to quench any alkyl lithium. The crude mixture was heated on a steam bath with a nitrogen sweep to remove THF. After cooling, the residue was dissolved in 200 mL of diethyl ether and then washed with three 100 mL portions of water. The ether was removed by heating on a steam bath with a nitrogen sweep. The residue was transferred to Kugelrohr apparatus and was heated to 210° C. at 0.5 torr to remove lower boiling impurities. The product eventually set up as a waxy solid (4.6 gram, 93 percent of theory) analyzing as follows:

$^1$H NMR (CDCl$_3$)δ: 1.8–2.3 (multiplet 4H); 2.3–2.9 (multiplet, 4H); 6.6–7.4 (multiplet 24H);

$^{31}$P NMR (CDCl$_3$)δ: +14 PPM (Relative to 85 Percent H$_3$PO$_4$).

EXAMPLE 8

Preparation of 1,2-Bis[2-(dibenzylphosphino)ethyl]benzene (BENPEB)

A mixture of BEB (3.1 grams, 10.6 mmole) and tribenzylphosphine (8.1 grams, 26.5 mmole) was heated under nitrogen at 160° C. for 16 hours. The resulting crude bisquaternary salt was pulverized. Toluene (70 mL) was added to the powder and the mixture was refluxed for 30 minutes. The purified insoluble bisquaternary salt was removed by filtration. The bisquaternary salt was added to a small flask and suspended in 50 mL of glyme solvent such as ethylene glycol dimethylether. Lithium aluminum hydride (0.38 gram, 10 mmole) was added in small portions to the stirred mixture. The resulting mixture was heated to reflux under nitrogen for 3 hours. The crude mixture was then heated on a steam bath under a nitrogen sweep to remove the glyme solvent. After cooling, the mixture was suspended in ether and quenched dropwise with water to destroy unreacted hydride reagent. The resulting mixture was washed with 10 percent hydrochloric acid followed by water. The ether layer was then heated on a steam bath with a nitrogen sweep. The product was isolated as a white solid (1.5 grams, 27 percent yield) analyzing as follows:

$^1$H NMR (CDCl$_3$)δ: 1.1-1.8 (multiplet 4H); 2.2-2.8 (multiplet, 12H); 6.7-7.2 (multiplet 24H);

$^{31}$P NMR (CDCl$_3$)δ: +15 PPM (Relative to 85 Percent H$_3$PO$_4$).

EXAMPLE 9

Preparation of 1,2-Bis[2-(diphenylphosphino)-2-phenyl ethyl]-benzene

A 500-mL three-necked flask was equipped with a mechanical stirrer, pressure equalizing dropping funnel, thermometer, and a nitrogen atmosphere. This was charged with 75 mL of THF and diphenylbenzylphosphine (6.0 grams, 21.7 mmole), and the mixture was then cooled to −5° C. N-Butyl lithium (1.55 molar in hexane, 14 mL, 21.7 mmole) was added dropwise to the cold mixture. The resulting dark red solution was stirred at −5° C. for an additional hour. The mixture was then cooled to −78° C. A solution of α,α'-dichloro-o-xylene (1.75 grams, 10 mmole) in 50 mL of THF was added dropwise to the cold anion solution over 40 minutes. The mixture was stirred at −78° C. for an additional 2 hours, and then it was warmed to 25° C. for 2 more hours. The mixture was quenched with 2 mL of water. The crude mixture was warmed to 70° C. and swept with argon to remove solvent. The residue was treated with a mixture of 200 mL of toluene and 75 ml of 5 percent aqueous hydrochloric acid. The aqueous phase was separated from the toluene layer and discarded. The toluene layer was washed once with 100 mL of water. The toluene solvent was removed by heating to 70° C. at 100 torr under an argon stream. The residue was purified by removing the volatile impurities by distillation with the base temperature reaching 210° C. at 1 torr. The base product (2.6 grams) was an amorphous yellow solid analyzing as follows:

$^1$H NMR (CDCl$_3$)δ: 2.37-2.93 (multiplet 14H); 3.33-3.78 (multiplet, 2H); 6.33-8.00 (multiplet 34H);

$^{31}$P NMR (CDCl$_3$): Two peaks at 0 ppm (Relative to 85 Percent H$_3$PO$_4$ diasteriomeric pair).

EXAMPLE 10

Preparation of 1,2-Bis[2-(dibenzylphosphino)-2-phenyl ethyl]benzene

This compound was prepared by a procedure very similar to that used in Example 9. Thus, tribenzylphosphine (12.2 grams, 40 mmole) was reacted with n-butyl lithium (1.55 molar, 28 mL, 43.4 mmole) to form the benzyl anion intermediate. This was reacted with α,α'-dichloro-o-xylene (3.5 grams, 20 mmole) to yield the 4.6 grams of product obtained as a water white viscous oil analyzing as follows:

$^1$H NMR (CDCl$_3$)δ: 2.50-3.43 (multiplet 14H); 6.93-7.67 (multiplet, 34H);

$^{31}$P NMR (CDCl$_3$): Two peaks at −2 ppm (Relative to 85 percent H$_3$PO$_4$ diasteriomeric pair).

The present hydroformylation process is carried out preferably in a gas sparged reactor such that the catalyst which is dissolved in a high boiling organic solvent under pressure does not leave the reaction zone with the aldehyde product which is taken overhead by the unreacted gases. The overhead gases are then chilled in a vapor liquid separator to condense out the aldehyde product, the gases being recycled to the reactor and the liquid product let down to atmospheric pressure for separation and purification by conventional techniques. A side draw from the reactor preferably is provided so that a small amount of the catalyst can be withdrawn at a desirable rate for more complete distillation and/or regeneration and returned to the reactor after the addition of make-up ligand thereto.

The metal catalyst components are charged preferably with solvent to the reactor through suitable pressurized pumping means, preferably in their soluble forms, e.g., their carboxylate salts or mineral acid salts or the like well known to the art as disclosed, for example, in U.S. Pat. No. 2,880,241. Charged therewith or separately is one or more of the present modifying ligands in amounts such that the molar ratio of ligand to rhodium in the reactor is from about 1.0 to about 200 or more, preferably from about 2.0 to about 10.0, and most preferably from about 2.3 to about 4.0.

In the process, the syn gas is introduced into the reactor in a continuous manner by means, for example, of a primary compressor, and the ratio of hydrogen to carbon monoxide in the feed may be selected according to the particular olefin being hydroformylated and the reaction conditions present, as is well known in the art. Generally, the molar ratio of hydrogen to carbon monoxide in the reactor is maintained within the range of about 0.5 to about 4.0, but it has been found in many hydroformylations that the rate of reaction as well as yield of the desired product may be increased by increasing the hydrogen to carbon monoxide molar ratio above 4.0, and up to about 10.0 or more. In the reactor zone the syn gas preferably is present in a molar excess (total moles of H$_2$+CO) with respect to the olefin and the molar ratio varies typically from about 0.5 to about 20, preferably from about 1.2 to about 6. In a liquid overflow reactor, the above molar ratio may have a lower limit of about 0.02.

The olefin is fed to the reactor by means of suitable pumps capable of operating under substantial pressures, and the feed rates of the olefin and syn gas are selected to maintain the above-recited molar ratios of these reactants in the reactor. Typical olefins to which the present invention is applicable include straight or branched chain α-olefins containing from 2 to 20 carbon atoms and preferably from 2 to 10 carbon atoms, and optionally containing groups or substituents which do not interfere with the hydroformylation process. Illustrative of such α-olefins are ethylene, propylene, 1-butene, 2-methylpropylene, 2-methyl-1-butene, 1-pentene, 1-hexene, 1-heptene, 1-octene, 2-ethyl-1-hexene, 1-dodecene, 1-octadecene, and allyl alcohol. If desired, mixtures of olefins, particularly ethylene and propylene, can be fed to the reactor. Alpha-olefins with heteroatom substitution on the molecule such as allyl alcohol, allyl acetate, 4-hydroxybutene-1, and the like may also be used as feedstocks. Also, branched olefins such as isobutene and internal olefins such as cis-butene-2, and diolefins such as 1,7-octadiene and the like may also be used to prepare dialdehyde products provided that the two carbon-carbon double bonds of the diolefin are not in conjugation.

Any suitable solvent which does not adversely affect the hydroformylation process and which is inert with respect to the catalyst, olefin feed, syn gas and the hydroformylation products may be used. Inert solvents of this nature are well known to those skilled in the art and include benzene, xylene, toluene and their substituted derivatives, pentanes, naphtha, kerosene, mineral oils, cyclohexane, cyclopentane, ethers, esters, etheresters, alcohols, acetals, ketones, and various mixtures thereof. Preferred solvents are those which are sufficiently high boiling to remain for the most part in the gas sparged reactor, and include 2,2,4-trimethyl-1,3-pentanediol monoisobutyrate (TMPDMI), and its isomers, and the by-products such as alcohols, hydroformylation reaction and retained as high boiling liquids at the bottom of the subsequent distillation columns.

Aldehyde product also may be prepared batchwise with the present invention by contacting the olefin, hydrogen, and carbon monoxide with the present catalyst in an autoclave. High boiling aldehyde products such as normal nonanal may be prepared in a continuous manner with the aldehyde product being removed from the reactor zone as a liquid in combination with the catalyst. The aldehyde product may be separated from the catalyst by conventional means such as by distillation, and the catalyst then recycled back to the reactor. It will be apparent to those skilled in the art that other reactor schemes may be used with this invention.

The present process can be carried out with very small amounts of catalyst containing from about $1 \times 10^{-6}$ moles of rhodium (calculated as Rh°) per mole of olefin in the reactor zone. However, such low catalyst concentrations are not commercially desirable since the reaction rates are low. The upper catalyst concentration is essentially unlimited and appears to be dictated principally by the high cost of rhodium and the fact that no advantage is evident in the use of catalyst containing above about $1 \times 10^{-1}$ moles of rhodium per mole of olefin in the reactor zone. A concentration of from about $1 \times 10^{-5}$ moles to about $5 \times 10^{-2}$ moles of rhodium per mole of olefin is preferred, and from about $1 \times 10^{-4}$ to about $1 \times 10^{-2}$ is most preferred.

EXAMPLE 11

Preparation of Rhodium 2-Ethylhexanoate Solution in Texanol ® Solvent

The apparatus consists of a 5-liter three-necked flask equipped with a heating mantle, Teflon bladed mechanical stirrer, reflux condenser, and a thermometer. Sodium hydroxide (80 grams) was dissolved in 1,000 ml of water in the flask. 2-Ethylhexanoic acid (196 grams) was added to the flask and dissolved. Rhodium chloride hydrate (42.62 grams containing 20 grams of rhodium metal value) was dissolved in 900 ml of water separately and then added to the stirred sodium 2-ethylhexanoate solution in the flask. The mixture was heated to 95° C. and kept vigorously stirred for 1.5 hours. A dark green oil of crude product separated. The mixture was cooled to room temperature and 400 ml of Texanol (2,2,4-trimethylpentane-1,3-diol-monoisobutyrate) solvent was added with stirring. The two phases were separated. The aqueous layer was reextracted with three 400 ml Texanol washes which were combined with the first organic extract. The combined organic phases were washed with 1,000 ml of water. The water wash was combined with the original water wash for rhodium analysis. The combined organic phases were filtered through a 0.5-inch thick bed of celite and made up to 2 liters volume with Texanol that was washed through the celite. The concentration of rhodium in the organic phase was 10,000 ppm and in the combined aqueous phase was 2 ppm.

EXAMPLE 12

Typical Bench-Scale Low Pressure Hydroformylation of Propylene Using The Present Catalysts The reactor consists of a vertically held stainless steel 4 foot by 1 inch (inside diameter) tube having a stainless steel filter element welded into its side near the bottom. The bottom of the tube has a drain valve and the top has a side port through which the vaporized products and unreacted gases leave the reactor. The top end of the tube is provided with a screwed plug which can be removed for charging the catalyst and which contains a thermowell whereby the temperature of the catalyst solution (reaction medium) in the reactor is measured accurately. Hydrogen and carbon monoxide are fed to the reactor from cylinders via pressure regulators and flow controllers which use differential pressure cells and air actuated flow control valves to maintain accurate flow. A third feed of nitrogen from a cylinder goes to the reactor via a pressure regulator and rotameter with needle valve. The carbon monoxide passes through a heated commercial "deoxo" unit as marketed by Engelhard Industries, Division, Engelhard Minerals and Chemicals Corp., Newark, N.J., to remove oxygen impurities. The nitrogen admixed with hydrogen pass through a similar "deoxo" unit before entering the reactor. Propylene is fed as a liquid to a preheater section or plenum chamber, where it is combined with the other feed gases and is vaporized prior to entering the reactor via the stainless steel filter element. The propylene feed rate is measured using rate-of-level drop in a tank containing liquid propylene using an armored rotameter with a needle valve to control the liquid propylene feed rate.

In operation, the catalyst is contained as a solution in the lower portion of the reactor tube and the reactant gases are sparged up through the solution as bubbles emanating from the filter element. Product butyraldehyde is formed in the catalyst solution where it accumulates and eventually is removed as a vapor by vapor/liquid equilibration with unreacted gases. This type of reactor is known as a vapor take-off or vapor stripped reactor. The hot gases are cooled upon leaving the reactor through said side port and the butyraldehyde product, along with some unreacted propylene, collects in a cooled high pressure separator connected by suitable conduit means to said side port. The noncondensed gases are let down to atmospheric pressure via a back pressure regulator which controls the reactor pressure. Additional butyraldehyde is condensed out of the atmospheric pressure gas stream by passing it through a series of three dry ice traps. Once an hour the contents of the high pressure separator and dry ice traps are collected and combined. The weight of butyraldehyde product obtained during the hour and its n/iso ratio are calculated using standard gas/liquid chromatographic techniques in combination with the crude weight of the product collected. In practice, approximately one hour is required for this bench unit to reach steady state production rates where catalyst activity and n/iso product ratio remain substantially constant.

Thus, a catalyst solution was prepared using $\alpha,\beta'$-bis(diphenylphosphino)ortho-ethyl toluene (BISHOP) (0.36 gram, 0.729 mmole) and rhodium 2-ethylhexanoate solution in Texanol solvent containing 31.25 mg (0.304 mmole) of rhodium as the metal were dissolved in 200 mL of Texanol solvent. The mixture was prepared under nitrogen and charged to the reactor under argon. The reactor was sealed, pressured and heated to 125° C. by an external oil bath with the gases sparging up through the catalyst. Propylene feed was started when the catalyst reached 125° C. The standard feed rates for this example and the examples presented in the tables are given in S.T.P. liters per minute, $H_2=CO=3.36$; $N_2=0.96$, propylene$=1.92$ as gas. The run was carried out a total of 5 hours. The reactor catalyst volume was kept at a standard operating level of 223 mL as measured by a calibrated D/P cell attached to the reactor. Texanol solvent was pumped in if the level dropped during the run. The average butyraldehyde production for the last 4 hours of operation was 59.6 grams per hour, equivalent to a catalyst activity of 4.20 pounds butyraldehyde per gram rhodium-hour (pounds butyraldehyde produced per gram of rhodium per hour) with a n/iso ratio of 5.89/1.

Table II is a summary of the results of bench-scale propylene hydroformylation runs employing chelating diphosphino ligands of the present invention according to the above hydroformylation procedure. The data of this table by comparison to the results of Table III show the importance of the relative ring positions of the phosphino alkyl groups, the $\alpha,\beta$ and $\beta,\beta'$ points of attachment of the alkyl groups to the phosphorus atoms, the desirability of having at least one aromatic group attached to each of the two phosphorus atoms, preferably two aromatic hydrocarbon groups attached to each phosphorus atom, and the desirability of having two hydrogen atoms attached to each of the carbon atoms of the alkyl chain which are directly bound to the two phosphorus atoms.

TABLE II

Effect of Ligand Structure on N/Iso Ratio and Catalyst Activity[1]

| Ligand[2] | Name Abbr. | L/Rh Mole Ratio | N/Iso Ratio | Oxo Act. lb HBu/g Rh-hr |
|---|---|---|---|---|
| (structure with Pφ2, Pφ2) | BISHOP | 2.4/1 | 5.89/1 | 4.20 |
| (structure with Pφ2, Pφ2) | DIPEB | 2.4/1 | 4.02/1 | 3.04 |
| (structure with PBz2, PBz2) | BENHOP | 2.4/1 | 3.61/1 | 1.03 |
| (structure with PBz2, PBz2) | BENPEB | 2.4/1 | 2.44/1 | 1.27 |

TABLE II-continued
Effect of Ligand Structure on N/Iso Ratio and Catalyst Activity[1]

| Ligand[2] | Name Abbr. | L/Rh Mole Ratio | N/Iso Ratio | Oxo Act. lb HBu/g Rh-hr |
|---|---|---|---|---|
| 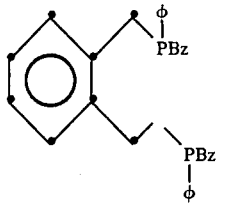 | PBENHOP | 2.4/1 | 5.75/1 | 4.39 |
| 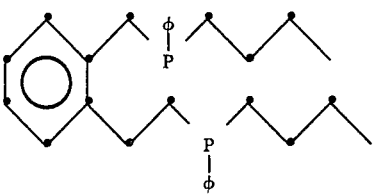 | PBUTHOP | 2.4/1 | 4.95/1 | 1.55 |
| 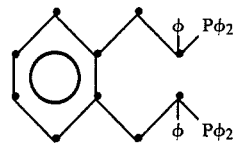 |  | 2.4/1 | 1.79/1 | 1.58 |
| 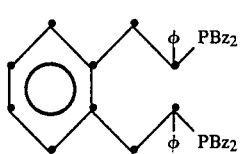 |  | 2.4/1 | 1.39/1 | 8.28 |

[1]All runs were carried out at 125 degrees C. using a 31.25 mg Rh charge at 260 psig with all the flows and operating conditions as stated in Example 12 with a ligand/rhodium mole ratio of 2.4/1.
[2]φ = phenyl, and Bz = benzyl.

TABLE III[a]

| Ligand | Catalyst Activity lb HBU/g Rh-hr | H Bu N/Iso Ratio |
|---|---|---|
| 1,8-DINAP[b] | 0.84 | 0.95/1 |
| Cis-1,2 DPCH[c] | 1.39 | 2.03/1 |
| O—XYL[d] | 3.10 | 2.41/1 |
| 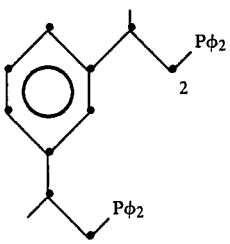 | 0.96 | 1.77/1 |
| 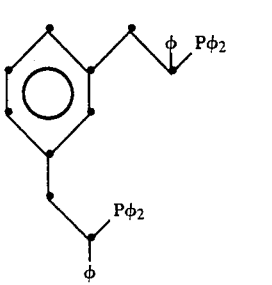 | 3.90 | 1.30/1 |
| 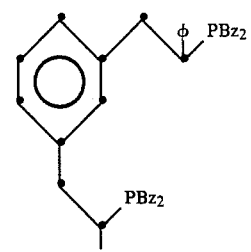 | 7.65 | 1.30/1 |

[a]Runs were conducted under same reaction conditions and reactant and catalyst concentrations as in Table II.
[b]1,8-Bis(diphenylphosphinomethyl) naphthalene.
[c]Cis-1,2-bis(diphenylphosphomethyl) 1,2-bis(diphenylphosphinomethyl) cyclohexane.
[d]α,α'-Bis(diphenylphosphino) ortho-xylene.

The invention has been described in detail with particular reference to preferred embodiments thereof, but it will be understood that variations and modifications can be effected within the spirit and scope of the invention.

We claim:
1. A ligand compound of the formula

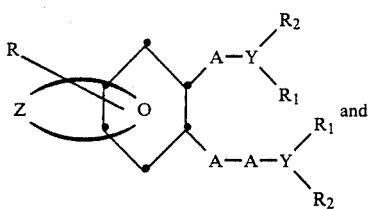

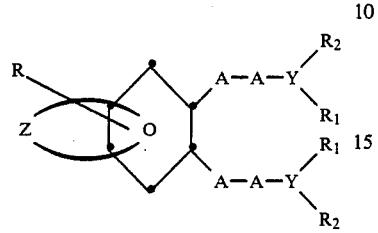

wherein

Z, when present, represents the atoms necessary to form with adjacent carbons on the benzene nucleus a fused divalent ring structure having up to about 20 ring carbons;

each ring is unsubstituted or substituted with up to three R substituents selected independently from alkyl, alkoxy, aryloxy, aryl, aralkyl, alkaryl, alkoxyalkyl, cycloaliphatic, halogen, alkanoyl, alkanoyloxy, alkoxycarbonyl, carboxyl or cyano;

each $R_1$ and $R_2$ is selected independently from alkyl, aryl, aralkyl, alkaryl or cycloaliphatic;

each A is a carbon atom which is either unsubstituted or substituted with one or two substituents selected independently from alkyl, alkoxy, aryloxy, aryl, aralkyl, alkaryl, alkoxyalkyl, cycloaliphatic, halogen, alkanoyl, alkanoyloxy, alkoxycarbonyl, carboxyl or cyano;

each of the above hydrocarbon groups or moieties of R, $R_1$ or $R_2$ may be substituted with 1-3 substituents selected independently from alkyl, alkoxy, aryloxy, aryl, aralkyl, alkaryl, alkoxyalkyl, cycloaliphatic, halogen, alkanoyl, alkanoyloxy, alkoxycarbonyl, carboxyl or cyano;

each of the above alkyl groups or moieties is straight or branched chain of 1-20 carbons, each aryl group contains 6-10 ring carbons, and each cycloaliphatic group contains from 4-6 ring carbons; and each Y is independently selected from the elements N, P, As, Sb and Bi.

2. A compound of claim 1 wherein each said alkyl group or moiety contains from 1-8 carbons.

3. A compound of claim 1 wherein the single hydrogens are unsubstituted, the "A" carbon hydrogens are unsubstituted, and $R_1$ and $R_2$ are each selected from phenyl or benzyl.

4. A compound of claim 1 of the structure

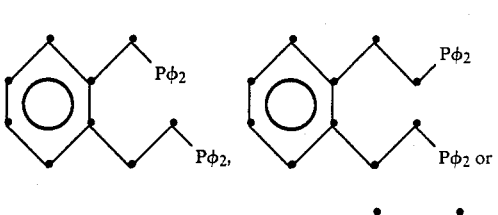

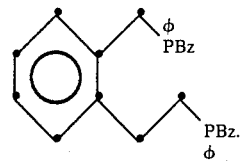

5. The catalyst comprising rhodium complexed with
(a) a ligand compound of claim 1 in a molar ratio of ligand/Rh of about 1,
(b) hydrogen in an atomic ratio of H/Rh of about 1, and
(c) carbon monoxide in a molar ratio of CO/Rh of about 2.

6. The catalyst according to claim 5 wherein the ligand has the structure

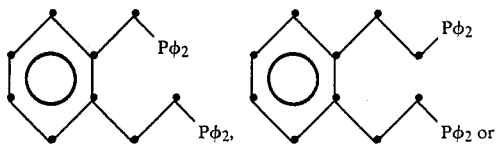

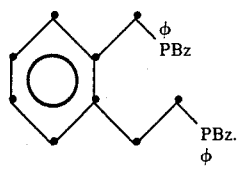

* * * * *